United States Patent [19]

Maurer et al.

[11] 4,291,572
[45] Sep. 29, 1981

[54] METHOD AND SYSTEM FOR CONTROLLING THE TEMPERATURE OF A HEAT MEASURING SENSOR ESPECIALLY IN MOTOR VEHICLES

[75] Inventors: Helmut Maurer, Schwieberdingen; Gerhard Dillman, Markgröningen; Franz Rieger, Aalen-Wasseralfingen; Ernst Linder, Mühlacker, all of Fed. Rep. of Germany

[73] Assignee: Robert Bosch GmbH, Stuttgart, Fed. Rep. of Germany

[21] Appl. No.: 165,922

[22] Filed: Jul. 3, 1980

Related U.S. Application Data

[63] Continuation of Ser. No. 924,407, Jul. 13, 1978, abandoned.

[30] Foreign Application Priority Data

Jul. 13, 1977 [DE] Fed. Rep. of Germany ....... 2731541

[51] Int. Cl.³ ............................................ G01N 27/12
[52] U.S. Cl. ............................................ 73/23; 60/276
[58] Field of Search ................... 73/23, 27 R; 60/276, 60/285; 123/440, 489

[56] References Cited

U.S. PATENT DOCUMENTS

| | | | |
|---|---|---|---|
| 3,973,529 | 8/1976 | Wessel et al. | 123/489 |
| 4,031,866 | 6/1977 | Asano | 123/489 |
| 4,033,170 | 7/1977 | Kawamura et al. | 73/23 |
| 4,106,451 | 8/1978 | Hattori et al. | 123/438 |
| 4,129,105 | 12/1978 | Ito et al. | 123/440 |
| 4,136,645 | 1/1979 | Ito et al. | 123/489 |

*Primary Examiner*—Stephen A. Kreitman
*Attorney, Agent, or Firm*—Edwin E. Greigg

[57] ABSTRACT

A method and system for controlling the temperature of a heat measuring sensor such as an oxygen sensor located in the exhaust line of an internal combustion engine so that the oxygen sensor will operate within optimal operating temperature. To accomplish this, a heating system including a control mechanism is provided for the oxygen sensor which adjusts the temperature of the oxygen sensor by controlling the output of a heater during the operation of the internal combustion engine according to characteristic engine operating conditions which have an effect on the temperature of the oxygen sensor, the most significant of which is engine load status. These conditions are sensed as a quantity by probes located so as to measure such operating conditions and send a signal to the control mechanism and its sensor heater.

10 Claims, 8 Drawing Figures

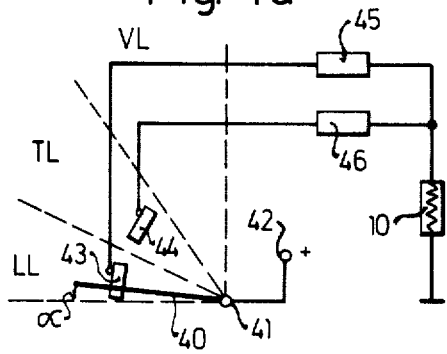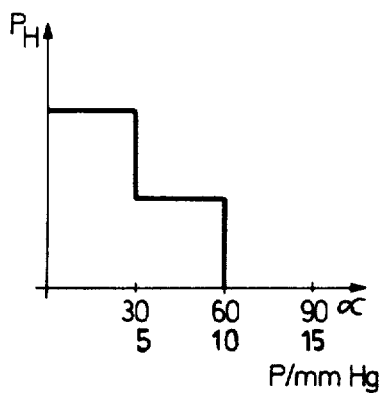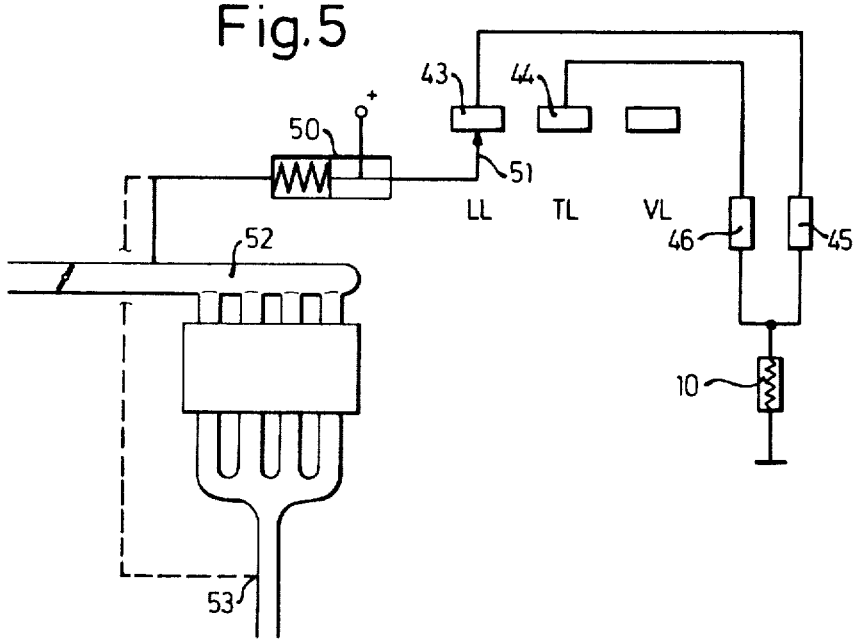

METHOD AND SYSTEM FOR CONTROLLING THE TEMPERATURE OF A HEAT MEASURING SENSOR ESPECIALLY IN MOTOR VEHICLES

This is a continuation, of application Ser. No. 924,407 filed July 13, 1978, now abandoned.

BACKGROUND OF THE INVENTION

This invention relates to heat sensors for installation in motor vehicles.

The prior art temperature measuring sensors for measuring the exhaust temperature for automotive vehicles utilized the internal resistance of the heat sensor itself to supply a signal representing the measured temperature since the conductivity of the sensor was extremely temperature-dependent. However, the disadvantage of this type of sensor was the expense involved to sense the change in conductivity of the internal resistance and the possible counter-influence of the sensor's measurement signal and the interior resistance measurement. This sometimes required an interruption of the current to insure that the correct measurement signal was being sent. Further, while it is known to include supplementary temperature probes within the measuring sensor itself and thus measure the temperature sensor with no intermediary device. It has also been found that this latter type of temperature measurement is very costly and, at present, the life expectancy of the measuring sensor is much shorter than that of the temperature probes and thus the device must be replaced often.

OBJECT AND SUMMARY OF THE INVENTION

Accordingly it is a primary object of this invention to provide a method and system of the above-described type wherein the heat measuring sensor for measuring the exhaust line temperature of an internal combustion engine is maintained at its optimal operating temperature.

It is another object of this invention to provide a method and system of the above-described type which has the advantages that the measurement sensor circuit need not be interrupted or supplementary elements need not be included within the measuring sensor.

These objects are obtained according to the invention by adjusting the temperature of the oxygen sensor to its optimal operating temperature according to the characteristic operating quantities of the internal combustion engine which have a significant influence over the sensor temperature, the most significant of which is the load status of the engine.

Thus, a more particular object of the invention is to use the load status of the internal combustion engine to adjust the measuring sensor temperature.

The invention will be better understood as well as further objects and advantages thereof will become more apparent from the following detailed description of the exemplary embodiments taken in conjunction with the drawings.

BRIEF DESCRIPTION OF THE DRAWINGS

FIG. 4a shows a control installation for the heating system which is dependent on the angle of a throttle valve, and FIG. 4b is a graph showing the relationship between throttle valve angle and sensor heater output; and FIG. 5 is a schematic illustration of a control installation which is actuated by the intake pressure and/or the exhaust gas pressure in internal combustion engines.

DESCRIPTION OF THE PREFERRED EMBODIMENTS

Figure 1:
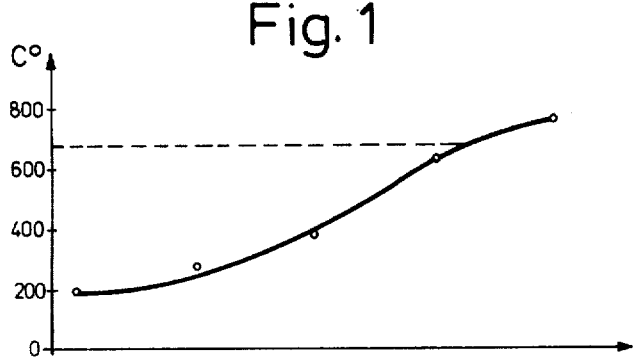
FIG. 1 is a graph showing the temperature of exhaust gas with respect to the operational load status of an internal combustion engine.

FIG. 1 shows the relationship between the engine load and the exhaust gas temperature in internal combustion engines. The significant temperatures shown are 200° C. at engine idling speed, approximately 400° C. in the mid-range of partial engine loading, and almost 800° C. at full engine load. The dotted horizontal line marking the temperature of about 680° C. indicates the optimal operating temperature of an oxygen measuring sensor. It can be seen from the curve that this optimal operating temperature of the oxygen sensor is first reached in the upper partial-load range, while under idling and lower partial-load conditions particularly in V-engines, the exhaust gas temperature at the point where a sensor could be installed is too low. The provision for a heating system for such a sensor which is adjustable according to engine load is therefore clearly needed.

Figure 2A:
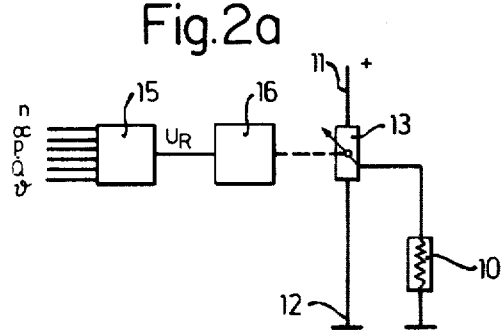
FIGS. 2a and 2b show two simplified schematic wiring diagrams of a sensor heating system.

FIG. 2a shows a simplified schematic wiring diagram of an oxygen sensor heating system installation. A heating element 10 is supplied with heat energy by means of a potentiometer 13 situated between a positive lead 11 and a negative lead 12. The control mechanism for the sensor heater is identified as 15 and it is equipped to receive, as for example, inputs for rpm, throttle valve angle and pressure rate of air flow in intake manifold and temperature. The control mechanism 15 produces an output voltage UR characterizing the particular temperature of the measuring sensor at the moment, which operates the potentiometer 13 through a switch means shown as block diagram at 16.

As to the installation of the invention, the indicated input quantities for the control mechanism 15 are given only as examples and need not all be utilized since the utilization of the load status alone is sufficient for temperature adjustment as may be seen in FIG. 1. By rpm herein is meant camshaft revolutions although the distributor shaft revolution may also be used, both of which are much lower in number at idling speed than in the full-load range. Too, the throttle valve angle α, or the pressure on the air flow rate in the intake manifold may also be utilized alone as an input to the control mechanism and the pressure signal P can be taken either at the intake side or the exhaust side of the engine. These locations may be selected because, as is well known, at idling speed there is a vacuum in the intake manifold and also a small pressure on the exhaust side of the engine, but at full load the amount of vacuum in the intake manifold is reduced and the pressure at the exhaust side is increased. However, in each installation of the invention it must be noted which location is chosen and the control mechanism 15 adjusted accordingly, and it is important to point out that a position near the sensor may be selected for temperature measurement by the probe, or a convenient point in the exhaust line may equally well be employed since the time delay involved is insignificant. It is, however, significant that temperature jumps of 250° per second can arise on the exhaust side of the internal combustion engine and for this reason a certain distance between exhaust valves and temperature sensor is practical.

Figure 2B:
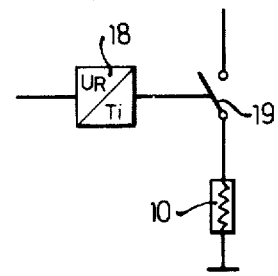

FIG. 2b shows a modification of the embodiment shown in FIG. 2a, where the control voltage UR is directed to a voltage-pulse width converter 18, which generates pulses $t_i$ that activate a switch 19, instead of potentiometer 13 of FIG. 2a, situated in the circuit of the heating element 10.

Figure 3A:
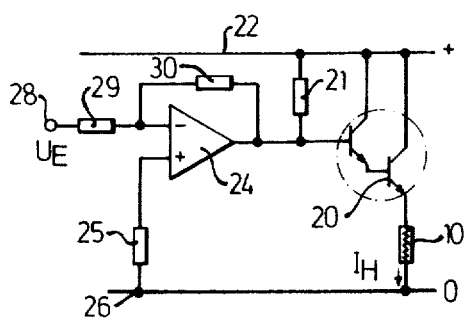
FIG. 3a shows a control installation for a sensor heating system in detail and FIG. 3b is a graph showing the relationship of input voltage and output current for the sensor heater.

FIG. 3a shows a detailed control installation with the heating element 10 and a transistorized emitter-follower circuit connected thereto to provide current IH for the heater 10. The input of the emitter-follower 20 is connected by a resistor 21 with a positive lead 22, as well as with the output of an inverse feedback circuit to differential amplifier 24. The positive input of the amplifier 24 is connected with a negative lead 26 through a resistor 25 while the negative input receives the input signal UE from input node 28 through input resistor 29. The inverse feedback resistor is identified as 30.

Figure 3B:
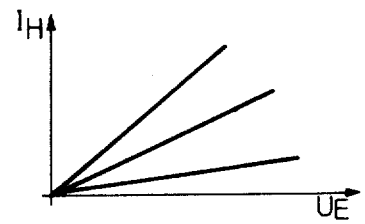

FIG. 3b shows the relationship between input voltage UE of the switching arrangement as in FIG. 3a and the current IH through heating element 10 depending upon the relationship of the selected resistance values for resistors 29 and 30 when wiring the amplifier 24 in the circuit as shown in FIG. 3a.

FIG. 4a shows an installation for oxygen sensor heating which is dependent in three states or steps of the throttle valve angle α for supplying current to the heating element 10. The throttle valve is shown here schematically as swivel arm 40 revolving about a pivotal axis 41. The swivel arm 40 is connected to a positive lead 42 and moves through relatively small angles making contact with two contact surfaces 43 and 44, which are connected with the heating element 10 through two different resistors 45 and 46. The contact surface 43 is situated in the idling range LL and thus is engaged at small throttle valve angles; the contact surface 44 is situated in the partial-load range TL and engaged at medium throttle valve angles; while the full-load range VL is given with large throttle valve angles, in which case there is no contact surface current supplied to the heating element.

FIG. 4b is a graph showing angles of the throttle valve in relation to heat generated by the heating system used with the arrangement shown in FIG. 4a. It can be seen that the heat generated by the heater 10 is stair-step in nature, and that in the idling range up to about a 30° throttle valve angle, LL in FIG. 4a, the maximum heating capacity of the heating element 10 is available, and is in the partial-load range between throttle valve angles of 30° and 60°, TL in FIG. 4a, half of the heating capacity is available, while in the full-load range at throttle valve angles between 60° and 90°, VL in FIG. 4a, there is no provision for heating the measuring sensor. The abscissa of the graph in FIG. 4b shows both an angle measurement scale and a pressure measurement scale P/mm Hg which symbolizes the pressure-dependent control of the heating system.

FIG. 5 finally shows a simplified schematic arrangement for a pressure-dependent control of the heating system. Again a three-stage heating control is provided as in the arrangement in FIG. 4a, but in this embodiment, the contact surfaces 43 and 44 are no longer engaged by a swivel arm but by a slider 51 which is actuated by a pressure converter 50. Input quantities of the pressure converter 50 may be either the pressure in the induction manifold 52 or as indicated by a dotted line by the pressure on the output side in the exhaust line 53 of the internal combustion engine. Contact pads which the slider 51 engages, are again connected to resistors 54 and 56. Thus, the heating capacity of heating element 10 is determined so that the highest heat production is achieved at idling speeds and none at full load as in FIG. 4a.

In addition to the control arrangements suggested above for the heat capacity of heating elements for measuring sensors, it is possible, where internal combustion machines in motor vehicles have continuously operating injection systems, to use the control pressure in the fuel circuit or the fuel adjustment circuit as the control value for the heating capacity.

The foregoing relates to preferred exemplary embodiments of the invention, it being understood that other embodiments and variants thereof are possible within the spirit and scope of the invention, the latter being defined by the appended claims.

What is claimed and desired to be secured by Letters Patent of the United States is:

1. A temperature control for a measuring sensor located in the exhaust gas line of an internal combustion engine of an automotive vehicle comprising:
   a measuring means,
   a heating element for controlling the temperature of said measuring means;
   a plurality of control mechanisms including said measuring means for measuring a control quantity and being selectively coupled in series with said heating element for determining at least three ranges including a variable heating performance at least at idling range and at partial-load range;
   means selecting one of said plurality of said control mechanisms including said measuring means, said selecting means selecting a selected characteristic operating quantity of said engine load including air flow rate measurement connecting one of said selected control mechanisms to said heating element for controlling the variable heat output of said heating element according to the measured quantity in at least two of said ranges, said automotive vehicle including a throttle valve rotatably fixed to move in an arc by a vehicle operator;
   means responsive to the position of said throttle valve to provide a stepped signal output; and
   means for receiving said stepped signal output to vary the heat output of said heating element.

2. The temperature control as claimed in claim 1, wherein the characteristic operating quantities of said internal combustion engine further comprises: the pressure in the exhaust manifold, the pressure in the exhaust line, the revolutions per minute of its camshaft, the revolutions per minute of its distributor shaft, the pressure in its intake manifold, the air flow rate in its intake manifold, the temperature in its exhaust line, and
   wherein said control mechanism includes at least one sensor probe to measure at least one said operating quantity.

3. The temperature control mechanism as claimed in claim 1, wherein said means for measuring said quantity includes a probe for measuring the pressure in the intake manifold.

4. The temperature control mechanism as claimed in claim 1, wherein said means for measuring said quantity includes a probe for measuring the air flow rate in said intake manifold.

5. The temperature control as claimed in claim 1, wherein said means for measuring said quantity includes means for measuring the temperature in the exhaust line.

6. The temperature control as claimed in claim 1, wherein said control mechanism includes a voltage responsive converter responsive to said measuring means;
switching means connected to said voltage responsive converter which opens and closes in response to the voltage output from said converter.

7. A temperature control for a measuring sensor located in the exhaust gas line of an internal combustion engine of an automotive vehicle comprising:
a measuring means,
a heating element for controlling the temperature of said measuring means;
a plurality of control mechanisms including said measuring means for measuring a control quantity and being selectively coupled in series with said heating element for determining at least three ranges including a variable heating performance at least at idling range and at partial-load range;
means selecting one of said plurality of said control mechanisms including said measuring means, said selecting means selecting a selected characteristic operating quantity of said engine load including air flow rate measurement connecting one of said selected control mechanisms to said heating element for controlling the variable heat output of said heating element according to the measured quantity in at least two of said ranges, said control mechanism including a differential amplifier having a negative input and a positive input, said negative input being connected to the output from said measuring means and said positive input being connected to vehicle ground;
a transistorized emitter-follower connected to the output of said differential amplifier; and
the input of said emitter-follower connected to the output of said differential amplifier;
the output of said emitter-follower being connected to said heating element whereby the current from said heating element is directly responsive to the voltage applied to the negative input of said differential amplifier.

8. The temperature control as claimed in claim 7, wherein a resistance means is coupled between said measuring means and said negative input of said differential amplifier, a second resistance means is located between vehicle ground and the positive input to said differential amplifier to vary the operating characteristics of said control mechanism.

9. A temperature control for a measuring sensor located in the exhaust gas line of an internal combustion engine of an automotive vehicle comprising:
a measuring means,
a heating element for controlling the temperature of said measuring means;
a plurality of control mechanisms including said measuring means for measuring a control quantity and being selectively coupled in series with said heating element for determining at least three ranges including a variable heating performance at least at idling range and at partial-load range;
means selecting one of said plurality of said control mechanisms including said measuring means, said selecting means selecting a selected characteristic operating quantity of said engine load including air flow rate measurement connecting one of said selected control mechanisms to said heating element for controlling the variable heat output of said heating element according to the measured quantity in at least two of said ranges, said control mechanism including a pressure responsive slide mechanism, said measuring means being connected to a source of pressure in said internal combustion engine, said slide mechanism being movable in response to the pressure measured by said measuring means, said slide mechanism also being connected to a source of positive voltage, a plurality of conductor pads and resistance means, one resistance means of a different value for each conductor pad and each connected in series with said heating element and vehicle ground, said slide mechanism including means for engaging said conductor pads one at a time for connecting said positive voltage source with said heating element and vehicle ground to vary the output of said heating element.

10. A temperature control for a measuring sensor located in the exhaust gas line of an internal combustion engine of an automotive vehicle comprising:
a measuring means,
a heating element for controlling the temperature of said measuring means,
at least one control mechanism including said measuring means for measuring a control quantity and being selectively coupled in series with said heating element for determining at least one range including a variable heating performance at least at idling range,
means selecting said at least one control mechanism including said measuring means, said selecting means selecting a selected characteristic operating quantity of said engine load including air flow rate measurement connecting said means selecting said at least one control mechanism to said heating element for controlling the variable heat output of said heating element according to the measured quantity in at least at idling range,
means rotatably fixed to move in an arc by a vehicle operator,
means responsive to the position of said rotatably fixed means to provide a stepped signal output, and
means for receiving said stepped signal output to vary the heat output of said heating element.

* * * * *